United States Patent [19]

Kirkland

[11] Patent Number: 4,639,251

[45] Date of Patent: Jan. 27, 1987

[54] FLEXIBLE COLLAPSIBLE CONTAINER WITH LIQUID LEVEL INDICATING DEVICE

[75] Inventor: W. Dean Kirkland, Walnut Creek, Calif.

[73] Assignee: KabiVitrum, Inc., Alameda, Calif.

[21] Appl. No.: 749,707

[22] Filed: Jun. 28, 1985

[51] Int. Cl.[4] .......................... A61M 5/00; G01F 23/00

[52] U.S. Cl. .......................................... 604/260; 222/50; 222/102; 116/227; 604/262

[58] Field of Search ............... 604/246, 257, 260, 262, 604/131; 116/227; 222/23, 49, 50, 95, 102

[56] References Cited

U.S. PATENT DOCUMENTS

| | | | |
|---|---|---|---|
| 2,083,603 | 6/1937 | Narwick | 222/95 |
| 2,734,662 | 2/1956 | Shippen | 222/102 |
| 3,777,697 | 12/1973 | Woessner | 116/227 |
| 4,088,166 | 5/1978 | Miller | 222/107 X |
| 4,090,541 | 5/1978 | Cammartata, III et al. | 222/107 X |
| 4,096,897 | 6/1978 | Cammartata, III | 222/107 X |
| 4,368,729 | 1/1983 | Dossin | 604/410 |
| 4,368,765 | 1/1983 | Larkin et al. | 604/408 |
| 4,465,487 | 8/1984 | Nakamura et al. | 604/408 |
| 4,516,977 | 5/1985 | Herbert | 604/415 |
| 4,551,139 | 11/1985 | Plaas et al. | 604/290 |

*Primary Examiner*—Dalton L. Truluck

*Attorney, Agent, or Firm*—Pollock, VandeSande & Priddy

[57] ABSTRACT

Apparatus for administering medical liquids comprising a combination of a calibrated flexible bag and a liquid level indicating device for increasing the accuracy of measuring the level of liquids within the bag. The liquid level indicating device consists of a pair of spaced-apart elongated rollers which form a slot into which the upper part of the bag can be inserted. The rollers rest on the outside of the bag at about the upper level of liquid within the bag.

5 Claims, 5 Drawing Figures

FLEXIBLE COLLAPSIBLE CONTAINER WITH LIQUID LEVEL INDICATING DEVICE

BACKGROUND OF THE INVENTION

This invention relates to flexible collapsible plastic containers, also referred to herein as bags, for medical solutions such as are used in intravenous fluid therapy, and more specifically to such bags which are calibrated for determining the volume or rate of administering medical solutions.

The flexible plastic containers have many advantages over glass containers including reduced weight, lack of susceptibility to breakage, reduced storage space requirements, and the potential for gravity drainage of liquid from the bag without the need to replace the liquid removed from the bag with air.

The accurate measurement of the volume of liquid in a bag is very important in many instances. For example, it may be important in determining the volume of liquid administered, and thereby monitoring the rate of infusion of liquid, and in verifying infusion pump volume indications. As a result of these needs, bags provided with calibrations are available. However, there has been concern about the accuracy of the measurements of the volume of liquid within flexible plastic containers based on these calibrations. One of the difficulties of accurately measuring the volume of liquid occurs when no headspace air is present, because as the liquid is withdrawn, the bag simply collapses, the two opposing surfaces of that portion of the bag gradually being forced together. As will be described in more detail below, there is no well-defined air-liquid interface or meniscus, and consequently there is the high probability of making a significant error in determining the volume of liquid which remains in the bag on the basis of calibrations thereon. Currently, a reading based on the calibration of containers is dependent upon a discernible air-liquid interface, but such a reading will vary considerably with the volume of headspace air. For example, 3000 mL of fluid in a flexible film container measured 3200 mL with 5 mL of headspace air, but only 2300 mL with 150 mL of headspace air.

SUMMARY OF THE INVENTION

It is accordingly one object of this invention to provide an improved means for the accurate and precise determination of the volume of liquid in a collapsible container.

In accordance with this invention, there has been provided apparatus for administering medical liquids comprising the combination of a calibrated flexible container devoid of air space and a liquid level indicating device wherein said liquid level indicating device comprises a pair of spaced-apart parallel elongated members which define a slot adapted to accommodate the container when the container is at least partially collapsed, said elongated members being adapted to rest on the outer surfaces of the walls of said container and to be supported at approximately the level of the upper surface of liquid within the container by pressure exerted against the walls of the container by the liquid contained therein.

The use of the liquid level indicating device described herein in combination with a flexible container results in an increase in the reproducibility of reading the volume of liquid within the container, even where two or more individual take the readings, and provides an increased accuracy of measurements of liquid volume and flow rate determination.

DETAILED DESCRIPTION OF THE INVENTION

The collapsible containers, per se, which form a part of the invention, are not novel, and suitable containers are readily available. The only requirement is that the container be sufficiently flexible so that opposing sides readily come together when liquid is drained from the container by gravity. Typically useful plastic from which the bags may be made are the polyolefins, polyvinylchlorides, ethylvinylacetates, etc.

Figure 1:
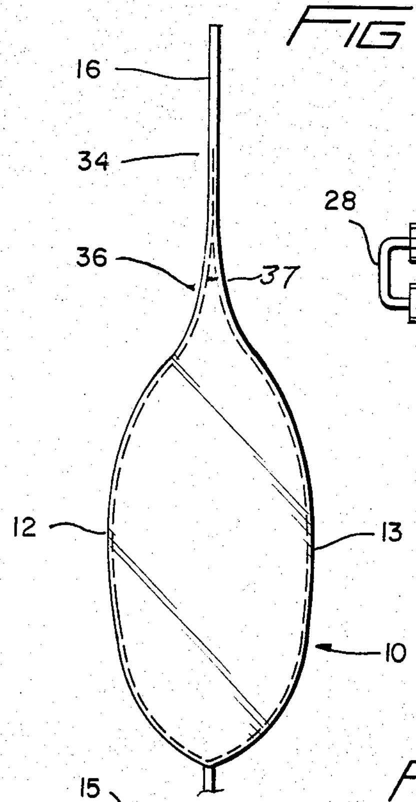
FIG. 1 is a view in elevation of a collapsible container in its typical position of use without the liquid level indicating device described herein.

FIG. 1 is a side view of plastic bag 10 formed by sealing the edges of planar plastic sheet 12 with the edges of planar plastic sheet 13. Handle 16 for supporting bag 10 in use is provided at the upper portion. As shown, the bag contains a liquid which has its upper surface 37, the meniscus, in the zone between 34 and 36. The position of the top surface of the liquid may vary depending on the volume of air space, yet its position is conventionally used to determine the apparent volume of liquid within the container. Errors arising from variations in the meniscus level for a typical container having a capacity of 3 liters may be as great as several hundred milliliters of liquid or more.

Figure 2:
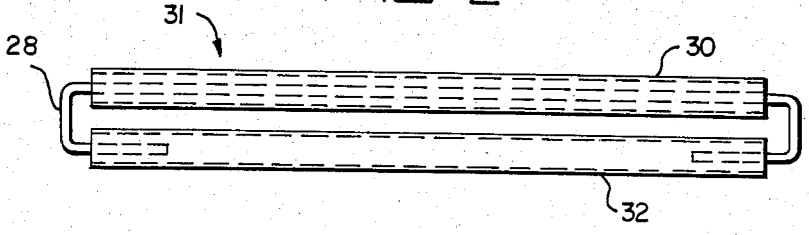
FIG. 2 is a plan view of the liquid level indicating device of this invention which, in combination with the collapsible container, provides improved accuracy and precision in measuring the volume of liquid within the container.
Figure 3:
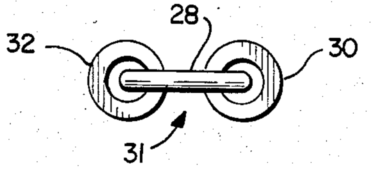
FIG. 3 is an end view of the device of FIG. 2.

FIGS. 2 and 3 show the preferred embodiment of the liquid level indicating device which makes possible an increase in the accuracy and precision of measuring the volume of liquid within the bag.

The preferred liquid level indicating device 31 comprises a pair of rollers 30, 32 which are spaced apart and mounted on axle means 28. The length of the rollers is not critical and rollers shorter than the width dimension of the bag may be used by sizing element 28 to span the width of the bag. However, the rollers are preferably long enough so that they fit easily over the collapsed bag, and most preferably have a length about equal to or slightly greater than the width of the collapsed bag. However, rollers significantly longer than the container width are also within the scope of the invention.

The spacing between the rollers must be great enough so that the flattened sheets 12, 13 in the collapsed portion of the bag will pass freely between the rollers, i.e., the spacing between the rollers should be slightly greater than the thickness of the two layers of film which make up the bag. Inasmuch as it may be necessary when assembling the bag and the liquid level indicating device for the rollers 30, 32 to pass over a handle, such as handle 16, when assembling the bag and the rollers, the spacing between the rollers should be sufficient to accommodate an increased thickness of plastic at that point. Typically useful spacing of the rollers is from about $\frac{1}{8}$ inch to about $\frac{3}{8}$ inch.

While the spacing between the rollers of the device 31 is not critical, it may affect the relative vertical positions of the rollers 30, 32 and volume reading, and it may be necessary in some instances to calibrate the collapsible bag with the specific device being used, or one having appropriate dimensions.

Figure 4:
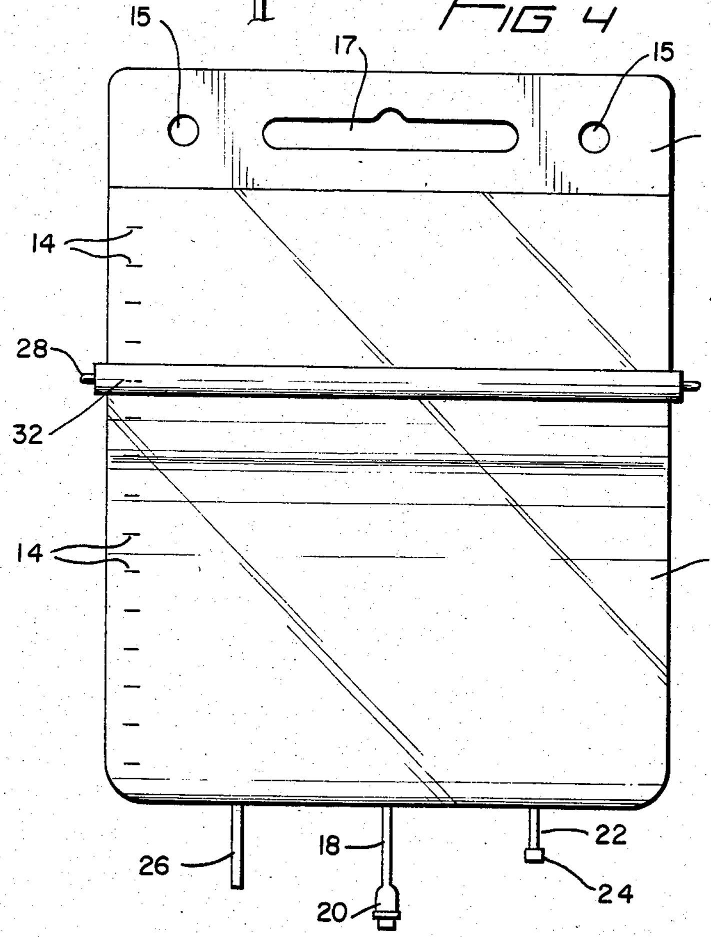
FIG. 4 is a front view of a collapsible container with the device of FIGS. 2 and 3 in place.
Figure 5:
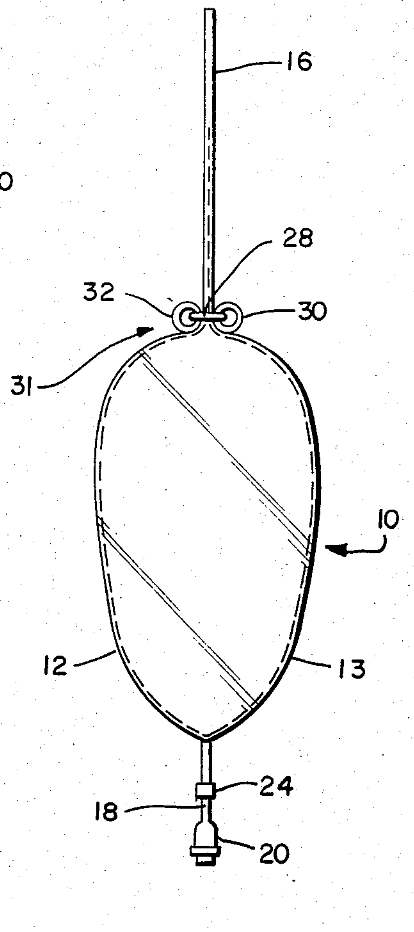
FIG. 5 is a side view of the container of FIG. 4.

As shown in FIGS. 4 and 5, bag 10 is provided with liquid level indicating device 31. Bag 10 is provided with handle 16 having openings 15 and 17 for suspending the container in use. Also shown in FIGS. 4 and 5 are fluid outlet means 26, inlet means 18 and 20, and injection port means 24 and 22. Front face 12 is provided with calibrations 14.

As shown in FIG. 5, planar sheets 12 and 13 are sufficiently close together in the zone above device 31 so that little or no liquid is present above the line of contact between rollers 32, 30 and plastic sheets 12 and 13, respectively. Therefore, device 31 provides a positive and reproducible reference point for reading the level of liquid within the flexible container 10.

While in the preferred embodiment of device 31 as shown in the Figures, the elements 30 and 32 are shown as cylindrical bodies, the invention also contemplates the use of other forms for these elements. For example, elements may be used which have a rectangular cross-section and which would not roll but instead would be capable of sliding downwardly on the outer surface of the plastic bag from the force of gravity as liquid is administered.

The diameters of the elements 30, 32 are not critical; however, elements having diameters in the range from about $\frac{1}{4}$ inch to about $\frac{1}{2}$ inch are preferred.

When properly sized, there is no need to force device 31 downwardly as liquid is administered, but it should just be permitted to follow the liquid surface down by virtue of gravity as liquid is removed from the bag.

In the preferred apparatus, all air is excluded from the bag. However, the invention also contemplates the use of the liquid level indicating device with bags containing air in such small quantities that the accuracy of measuring the volume of liquid in the bag is not significantly reduced.

Having thus described the invention, the following example is given to illustrate it in more detail.

EXAMPLE

An intravenous collapsible container as shown in the Figures having a capacity of 3000 milliliters and dimensions when collapsed of about $9\frac{1}{2}$ inches by about 11 inches, was fitted with a device 31 having steel rollers made from hollow tubing which were about $10\frac{1}{8}$ inches long, about $\frac{3}{8}$ inch in outside diameter, about $\frac{1}{4}$ inch in inside diameter and having a space between them of about 5/32 inch. The element 28 was a steel wire about 3/32 inch in diameter which enters through element 30 and was bent to extend about $\frac{1}{2}$ inch into each end of element 32.

What is claimed is:

1. Apparatus for administering medical liquids comprising the combination of a calibrated flexible collapsible container and a liquid level indicating device which is supported on the outside surface of the calibrated container at about the upper level of the liquid contained therein wherein said collapsible container contains a liquid and is substantially devoid of air and said liquid level indicating device comprises a pair of spaced-apart, parallel elongated members which define a narrow rectangular slot, said slot being sized so that when a collapsed portion of the container is inserted therein opposing surfaces of said container are urged into abutting relationship with each other at about the level of the upper surface of liquid within the container.

2. Apparatus according to claim 1 wherein the elongated members comprise hollow tubing.

3. Apparatus according to claim 1 wherein the elongated members are cylindrical and rotatable about their axes.

4. Apparatus according to claim 1 wherein the liquid level indicating device comprises a pair of cylindrical elongated members, each having a diameter from about $\frac{1}{4}$ inch to about $\frac{1}{2}$ inch and are spaced apart at their maximum span from about $\frac{1}{8}$ inch to about $\frac{3}{8}$ inch.

5. Apparatus according to claim 1 wherein said collapsible container comprises two opposing sheets of flexible plastic having their abutting edges sealed together to form an enclosed volume for retaining liquid to be administered.

* * * * *